(12) United States Patent
Safinya et al.

(10) Patent No.: US 6,899,895 B2
(45) Date of Patent: May 31, 2005

(54) LAMELLAR GELS AND METHODS FOR MAKING AND REGULATING

(75) Inventors: Cyrus R. Safinya, Santa Barbara, CA (US); Heidi E. Warriner, Goleta, CA (US); Stefan H. J. Idziak, Waterloo (CA)

(73) Assignee: The Regents of the University of California, Oakland, CA (US)

( * ) Notice: Subject to any disclaimer, the term of this patent is extended or adjusted under 35 U.S.C. 154(b) by 529 days.

(21) Appl. No.: 09/754,509

(22) Filed: Jan. 4, 2001

(65) Prior Publication Data

US 2001/0012520 A1 Aug. 9, 2001

Related U.S. Application Data

(63) Continuation of application No. 09/023,262, filed on Feb. 13, 1998, now Pat. No. 6,207,186.
(60) Provisional application No. 60/037,944, filed on Feb. 14, 1997.

(51) Int. Cl.$^7$ .............................................. A61K 9/127
(52) U.S. Cl. ...................................... 424/450; 424/401
(58) Field of Search ............................... 424/450, 1.21, 424/9.321, 9.51, 417; 428/402.2; 264/4.1, 4.3; 436/829; 135/59

(56) References Cited

U.S. PATENT DOCUMENTS

| | | | |
|---|---|---|---|
| 4,774,085 A | | 9/1988 | Fidler |
| 5,013,556 A | * | 5/1991 | Woodle |
| 5,288,499 A | | 2/1994 | Janoff et al. |
| 5,374,715 A | * | 12/1994 | Kanno |
| 5,741,513 A | * | 4/1998 | Ghyczy |
| 5,882,679 A | * | 3/1999 | Needham |

OTHER PUBLICATIONS

Behr, Jean Paul, "Gene Transfer with Synthetic Cationic Amphiphiles: Prospects for Gene Therapy," B*ioconjugate Chem*, 5:382–389. 1994 (Exhibit 3).
Radler, Joachim et al., "Structure of DNA–Cationic Liposome Complexes: DNA Intercalation in Multilamellar Membranes in Distinct Interhelical Packing Regimes," *Science*, 275:810–814. Feb 7, 1997 (Exhibit 4).
Felgner, P. L. and G. Rhodes, "Gene Therapeutics," *Nature*, 349:351–352. Jan. 24, 1991 (Exhibit 5).
Felgner, P. L. et al., "Lipofection: A highly efficient, lipid–mediated DNA–transfection procedure," *Proc. Natl. Acad. Sci. USA*, 84:7413–7417. Nov. 1987 (Exhibit 6).

Remy, Jean–Serge et al., "Targeted gene transfer into hepatoma cells eith lipopolyamine–condensed DNA particles presenting galactose ligands: A stage toward artificial viruses," *Proc. Natl. Acad. Sci. USA*, 92:1744–1748. Feb. 1995 (Exhibit 7).
Zhu, Ning et al., "Systemic Gene Expression After Intravenous DNA Delivery into Adult Mice," *Science*, 261:209–211. Jul. 9, 1993 (Exhibit 8).
Remy, Jean–Serge et al., "Gene Transfer with a Series of Lipophilic DNA–Binding Molecules," *Bioconjugate Chem.*, 5:647–654. 1994 (Exhibit 9).
Felgner, Jiin H. et al., "Enhanced Gene Delivery and Mechanism Studies with a Novel Series of Cationic Lipid Formulations," *The JOurnal of Biological Chemistry*, 269(4):2550–2561. 1994 (Exhibit 10).
Farhood, Hassan et al., "The role of dioleoyl phosphatidylethanolamine in cationic liposome mediated gene transfer," *Biochemica et Biophysica Acta*, 1235:289–295. 1995 (Exhibit 11).
Hui, Sek Wen et al., "The Role of Helper Lipids in Cationic Liposome–Mediated Gene Transfer," *Biophysical Journal*, 71:590–599. Aug. 1996 (Exhibit 12).
Chiang, Ming–Yi et al., "Antisense Oligonucleotides Inhibit Intracellular Adhesion Molecule 1 Expression by Two Distinct Mechanism," *The Journal of Biological Chemistry*, 266(7):18162–18171. Sep. 25, 1991 (Exhibit 13).
Lappalainen, Katriina et al., "Cationic liposomes improve stability and intracellular delivery of antisense oligonucleotides into CaSki cells," *Biochemica et Biophysica Acta*, 1196:201–208. 1994 (Exhibit 14).
Seddon, John M., "Structure of the inverted hexagonal ($H_{II}$) phase, and non–lamellar phase transition of lipids," *Biochemica et Biophysica Acta*, 1031:1–69. 1990 (Exhibit 15).
Boltenhagen, Ph. et al., "Focal conic domains with positive Gaussian curvature and saddle–splay rigidity of smectic $L_\alpha$ phases," *Physical Review A*, 46(4):R1743–R1746. Aug. 15, 1992 (Exhibit 16).
Gruner, Sol M., "Stability of Lyotropic Phases with Curved Interfaces," *J. Phys. Chem.*, 93:7562–7570. 1989 (Exhibit 17).
Antonietti, Markus et al., "Polyelectrolyte–Surfactant Complexes: A New Type of Solid, Mesomorphous Material," *Macromolecules*, 27:6007–6011. 1994 (Exhibit 18).

* cited by examiner

*Primary Examiner*—Gollamudi S. Kishore
(74) *Attorney, Agent, or Firm*—Mandel & Adriano

(57) ABSTRACT

The invention provides novel compositions involving lamellar gels and methods for making them. These compositions and methods of the invention are significant improvements in the field of gels, macromolecular targeting and macromolecular delivery to various biological systems.

21 Claims, 5 Drawing Sheets

LAMELLAR GELS AND METHODS FOR MAKING AND REGULATING

This application is a continuation application of U.S. Ser. No. 09/023,262, filed Feb. 13, 1998, now U.S. Pat. No. 6,207,186 which claims the priority of U.S. Ser. No. 60/037,944, filed Feb. 14, 1997, the contents of which are hereby incorporated by reference in its entirety.

Throughout this application various publications are referenced. The disclosures of these publications in their entireties are hereby incorporated by reference into this application in order to more fully describe the state of the art to which this invention pertains.

BACKGROUND OF THE INVENTION

The field of the invention is lamellar gels and methods for making and using thereof.

Gels are viscoelastic materials that normally consist of a solid component dispersed in a liquid, water in the case of hydrogels. Polymer gels, either natural such as gelatin, or synthetic, contain a polymer network that serves as the solid component and can resist shear. For many biological applications, gels based on high molecular weight polyethylene glycol have been used because of their low immunogenicity. In this context these gels coat more immunogenic tissues, proteins and other materials and thereby provide protection from immune response.

Conventional polymer gels incorporate solid phase components, a characteristic that places constraints on their manipulation and use in a variety of settings. Polymer gels that incorporate solid phase components (e.g., poly(vinyl alcohol) based gels) (1) are severely limited in their ability to provide flexible means for making reagents accessible to or directing such reagents towards different targets.

Gels that can function without solid phase components such as those that utilize a lamellar hydrogel phase for regulating their viscosity and elasticity would overcome many of the problems observed in the field of conventional gels. Unlike polymer gels that incorporate a primarily covalently-linked network with no fluid component, a bioactive gel such as the gel of the invention, based on fluid membranes could incorporate membrane-imbedded proteins or other biologically active molecules, thus providing a way to deliver such molecules in a stable gel.

The state of the current art in the field of gels (polymer gels) and their compositions and methods for making and using in a manner that facilitates drug targeting and delivery or other applications for molecule delivery in related contexts, is limited by the inability to imbed molecules into the linked network.

The present invention is directed to overcoming the limitations associated with polymer gels.

SUMMARY OF THE INVENTION

The invention provides novel compositions involving lamellar gel complexes and methods for making them. This new class of fluid membrane based compositions and methods of the manipulating them are significant improvements in the field of gel complex synthesis, macromolecule targeting and delivery to various biological systems.

The disclosed invention utilizes novel compositions of materials and identifies critical material parameters in the method of controlling lamellar gel formation and component parameters, e.g., controlling the characteristics of the gel superstructure. In addition, the invention disclosed means to manipulate the phase structure of the lamellar gel compositions in order to facilitate their use in molecule targeting and delivery.

By utilizing these new compositions and the methods for making, using and manipulating this new class of gels, an extremely versatile molecular targeting and delivery system can be developed for a variety of applications. The invention has applications in the numerous protocols, which would benefit from the utilization gels such as bioactive hydrogels partnered with various macromolecules. Such protocols include tissue healing as well as the molecular delivery of various molecules including drugs, peptide and proteins. The disclosed invention also has applications in the field of the so-called "smart" hydrogels (e.g., gels for therapeutic or cosmetic applications) of polymer networks that respond by altering their configurations to external stimuli such as temperature, solvent or pH changes.

DETAILED DESCRIPTION OF THE INVENTION

Definitions

Figures 1A, 1B:
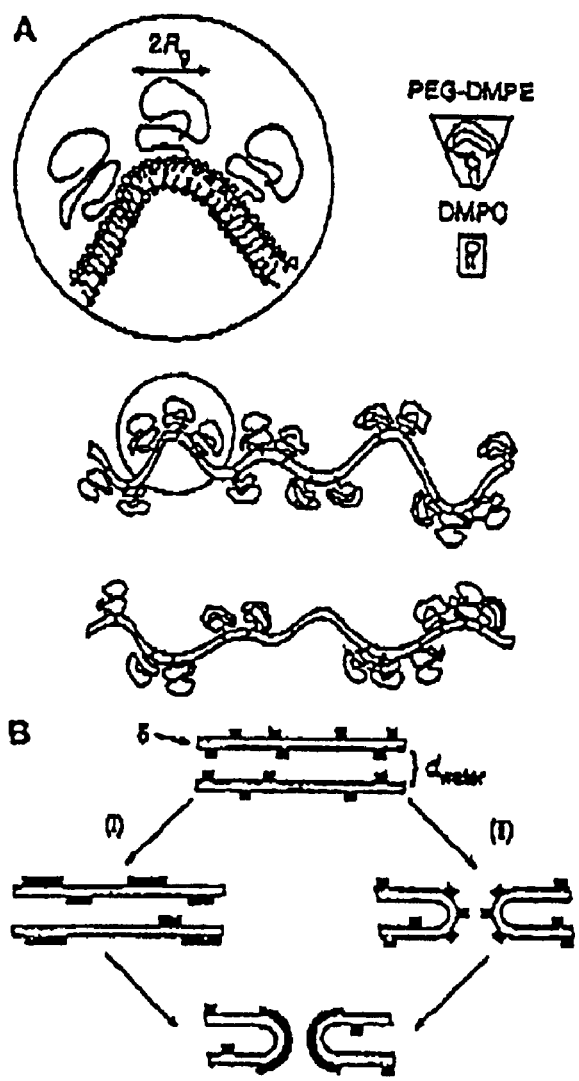
FIG. 1A is a schematic of two undulating fluid membranes of the lamellar gels of the invention [composed of DMPC and co-surfactant pentanol (single chain)] with PEG-lipid hydrophobically anchored but freely diffusing within the membrane.
FIG. 1B is a schematic of two paths that would form defects, with the laterally phase separated PEG-lipid residing in, and stabilizing, the regions of high curvature.

As used in this application, the following words or phrases have the meanings specified.

As used herein, the term "lipid" means any of various substances both biologically and non-biologically derived that are soluble in nonpolar solvents.

As used herein, the term "surfactant" means any of various substances that are surface-active.

As used herein, the term "sufficient amount" means a concentration of a given component that is determined to be adequate to produce the appropriate complex.

As used herein, the term "making" means constructing in a systematic, ordered, or other manner.

As used herein, the term "membrane associating particle" means a multifunctional compound composed of two or more substituents, which serves to associate the particle with a specific chemical environment such as the membrane.

As used herein, the term "membrane bending rigidity reducing reagent" means an agent that reduces membrane bending rigidity to accommodate curvature of the gel. Membrane bending rigidity is the elastic modulus that is a measure of the membrane bending stiffness.

In order that the invention herein described may be more fully understood, the following description is set forth.

Compositions of the Invention

The present invention provides the disclosure of novel lamellar gels constructed of (i) flexible membranes comprised of surfactants, lipids or combination thereof, (ii) a multifunctional membrane associating particle which anchors to the membrane and may create a highly curved membrane region and, optionally, (iii) an agent that reduces the membrane bending rigidity.

In the disclosed invention, the membrane associating particle (also referred herein as MAP) with the flexible membrane creates the resulting lamellar gel phase. The MAP creates the highly curved membrane regions of the gel that breaks up the multilamellar phase into smaller multilamellar domains. This curvature results when a head area to tail area ratio of the MAP becomes increasingly greater than one (13). The membrane must be either inherently flexible or incorporate a membrane rigidity reducing reagent to accommodate this resulting curvature. The highly packed multilamellar domains that result from such compositions then give rise to the viscolelastic properties of the lamellar gel.

In one embodiment of the invention, the lamellar membranes are composed of the lipid dimyristol phosphatidyl choline. This membrane forming lipid is one of a large class of surfactants and lipids (and combinations thereof) which may be utilized in this context to form the membranes of the invention.

Examples of suitable lipids, which are neutral, include but are not limited to: dioleoyl phosphatidyl cholin, 1,2-dioleoyl-sn-glycero-3-phosphoethanolamine, 1,2-dicaproyl-sn-glycero-3-phosphoethanolamine, 1,2-dioctanoyl-sn-glycero-3-phosphoethanolamine, 1,2-dicapryl-sn-glycero-3-phosphoethanolamine, 1,2-dilauroyl-sn-glycero-3-phosphoethanolamine, 1,2-dimyristoyl-sn-glycero-3-phosphoethanolamine, 1,2-dipentadecanoyl-sn-glycero-3-phosphoethanolamine, 1,2-dipalmitoyl-sn-glycero-3-phosphoethanolamine, 1,2-diphytanoyl-sn-glycero-3-phosphoethanolamine, 1,2-dipalmitoleoyl-sn-glycero-3-phosphoethanolamine, 1,2-distearoyl-sn-glycero-3-phosphoethanolamine, 1,2-dipretrselinoyl-sn-glycero-3-phosphoethanolamine, 1,2-dielaidoyl-sn-glycero-3-phosphoethanolamine, 1,2-dilauroyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-docosahexaenoyl-sn-glycero-3-phosphoethanolamine, 1,2-myristoleoyl-sn-glycero-3-phosphocholine, 1,2-dimyristelaidoyl-sn-glycero-3-phosphocholine, 1,2-palmitoleoyl-sn-glycero-3-phosphocholine, 1,2-palmitelaidoyl-sn-glycero-3-phosphocholine, 1,2-petroselinoyl-sn-glycero-3-phosphocholine, 1,2-dioleoyl-sn-glycero-3-phosphocholine, 1,2-dielaidoyl-sn-glycero-3-phosphocholine, 1,2-dilinoleoyl-sn-glycero-3-phosphocholine, 1,2-linoleoyl-sn-glycero-3-phosphoethanolamine, 1,2-eicosenoyl-sn-glycero-3-phosphoethanolamine, 1,2-arachidonoyl-sn-glycero-3-phosphoethanolamine, 1,2-erucoyl-sn-glycero-3-phosphocholine, 1,2-nervonoyl-sn-glycero-3-phosphocholine, 1,2-propionoyl-sn-glycero-3-phosphocholine, 1,2-butyroyl-sn-glycero-3-phosphocholine, 1,2-valeroyl-sn-glycero-3-phosphocholine, 1,2-caproyl-sn-glycero-3-phosphocholine, 1,2-heptanoyl-sn-glycero-3-phosphocholine, 1,2-capryloyl-sn-glycero-3-phosphocholine, 1,2-nonanoyl-sn-glycero-3-phosphocholine, 1,2-capryl-sn-glycero-3-phosphocholine, 1,2-undecanoyl-sn-glycero-3-phosphocholine, 1,2-lauroyl-sn-glycero-3-phosphocholine, 1,2-tridecanoyl-sn-glycero-3-phosphocholine, 1,2-myristoyl-sn-glycero-3-phosphocholine, 1,2-pentadecanoyl-sn-glycero-3-phosphocholine, 1,2-palmitoyl-sn-glycero-3-phosphocholine, 1,2-phytanoyl-sn-glycero-3-phosphocholine, 1,2-heptadecanoyl-sn-glycero-3-phosphocholine, 1,2-stearoyl-sn-glycero-3-phosphocholine, 1,2-bromostearoyl-sn-glycero-3-phosphocholine, 1,2-nonadecanoyl-sn-glycero-3-phosphocholine, 1,2-arachidoyl-sn-glycero-3-phosphocholine, 1,2-heneicosanoyl-sn-glycero-3-phosphocholine, 1,2-behenoyl-sn-glycero-3-phosphocholine, 1,2-tricosanoyl-sn-glycero-3-phosphocholine, 1,2-lignoceroyl-sn-glycero-3-phosphocholine.

Additional examples of suitable lipids, which are charged, include, but are not limited to, 1,2-diacyl-3-trimethylammonium-propane, 1,2-dimyristoyl-3-trimethylammonium-propane, 1,2-dipalmitoyl-3-trimethylammonium-propane, 1,2-distearoyl-3-trimethylammonium-propane, 1,2-diacyl-3-dimethylammonium-propane, 1,2-dimyristoyl-3-dimethylammonium-propane, 1,2-dipalmitoyl-3-dimethylammonium-propane, 1,2-distearoyl-3-dimethylammonium-propane, and 1,2-dioleoyl-3-dimethylammonium-propane.

Examples of suitable surfactants include but are not limited to bis(2-ethyl-hexyl) sulfasuccinate or pentaethyleneglycol dodecyl ether.

In one embodiment of the invention, the MAP is composed of the polymer-lipid combination, 1,2-diacyl-sn-glycero-3-phosphoethanolamine-N-[poly(ethylene glycol)]. In this bifunctional combination, the polyethylene glycol [$PEO_x(OCH_2CH_2)_n$](PEG) serves to generate the highly curved membrane region while the lipid acts to anchor the MAP to the membrane.

Such membrane associating particles may be generated from a wide variety of constituents with the same basic properties. PEG 150 to PEGs with molecular weights greater than a million (as long as the gel is dilute enough with the solvent so as to fit the polymer between the membranes) are useful in the forming the curved regions, with PEGs in the range of 150 to 15,000 being preferable with about 2000 to about 5000 being most preferable (Avanti Polar Lipids, Inc.)

As to the curvature generating portion of the membrane associating particle, a number of molecules may be substituted for PEG, including non polymers such as colloidal particles or magnetic particles having a head area to tail area greater than 1. In addition, MAPs may include other known biopolymers such as proteins and nucleic acids or known chemical polymers such as polyvinyl-alcohol and the like having the ability to induce curvature of the lipid membrane. Those skilled in the art will appreciate means to identify and distinguish such molecules (i.e., head area/tail area is greater than one (1)). See "Advanced Organic Chemistry: Reactions, Mechanisms and Structure", 3rd Edition (Wiley and Sons, 1985) incorporated by reference herein.

As to the anchor portion of the MAP, i.e. the portion that attaches to the lipid membrane, a number of molecules may be substituted for the lipid, 1,2-diacyl-sn-glycero-3-phosphoethanolamine. A great number of hydrophobic molecules will serve to anchor the particle in a nonpolar membrane including other nonpolar membrane associating lipids (e.g., in membranes of the lipid dimyristoyl phosphatidyl choline). Those skilled in the art will appreciate means to identify and distinguish such molecules (e.g., based on the presence of a fat-soluble region of the molecule). See "Advanced Organic Chemistry: Reactions, Mechanisms and Structure", 3rd Edition (Wiley and Sons, 1985) incorporated by reference herein.

In one embodiment of the invention, the agent that reduces the membrane rigidity (i.e., the stiffness modulus) is an alcohol. There are a wide variety of alcohols that will serve to produce a flexible membrane (e.g., in the range of 1 $k_B T < K < 20 \, k_B T$). Medium chain alcohols from butanol to nonanol will function in this context, with pentanol, heptanol and hexanol being preferred. Additionally, biologically derived alcohols such as geraniol will also function in this manner.

The compositions of the invention are based on the interaction of fundamental constituents to create a lamellar gel phase. The relative amount of the various constituents varies in relation to the proportion of each additional functional constituent with the ratio of each constituent being obtained by the formula set out below.

In one embodiment, the lamellar gel composition is comprised of a flexible surfactant in a proportion sufficient to form a flexible membrane (14), a MAP in an amount sufficient to create a highly curved membrane region and water.

In another embodiment, the lamellar gel composition is comprised of at least one of a lipid, surfactant, or combination thereof in a proportion sufficient to form a flexible membrane, a MAP in an amount sufficient to create a highly curved membrane region (e.g., the amount is sufficient when G'>G") (FIG. 3), a membrane bending rigidity reducing reagent in an amount sufficient to reduce membrane bending rigidity and water.

In one of the embodiments of the lamellar gel composition, the lipid used to form a membrane is comprised of lipid dimyristol phosphatidyl choline.

In one of the embodiments of the lamellar gel composition, the lipid used to form a membrane is comprised of lipid is di-oleolyl phosphatidyl choline.

In one of the embodiments of the lamellar gel composition, the lipid used to form a membrane is comprised of lipid is di-oleolyl phosphatidyl ethanolamine.

In one of the embodiments of the lamellar gel composition, the lipid used to form a membrane is comprised of lipid is di-oleolyl phosphatidyl serine.

In one of the embodiments of the lamellar gel composition, the lipid used to form a membrane is comprised of lipid is di-oleolyl trimethylammonium propane.

In one of the embodiments of the lamellar gel composition, the MAP used to create a highly curved membrane region is PEG-1,2-diacyl-sn-glycero-3-phosphoethanolamine.

In one of the embodiments of the lamellar gel composition, the PEG in the MAP used to create a highly curved membrane region is PEG-2000. Alternatively, it can be PEG-5000.

In one of the embodiments of the lamellar gel composition, the membrane bending rigidity reducing reagent used to reduce membrane bending rigidity and water is an n-alcohol with 4 to 9 carbon molecules.

In one embodiment, the lamellar gel further comprises approximately 1–500 mM NaCl.

In one embodiment, the lamellar gel comprises an amount of water from approximately 60 to approximately 99%, at least one of a lipid and a surfactant in an amount from approximately 1 to approximately 40 weight %, approximately 0.5 to approximately 20 weight % of a MAP and approximately 2 to approximately 10 weight % of a membrane bending rigidity reducing reagent. These composition ranges are by no means limiting and other embodiments exist.

In one embodiment, the lamellar gel comprises 90.0 weight % water, 6.0 weight % lipid, 3.46 weight % pentanol and 0.54 weight % PEG-lipid. In yet another embodiment, the lamellar gel composition comprised 83.0 weight % water, 8.4 weight % lipid, 5.7 weight % pentanol and 3.0 weight % PEG-lipid. In yet another embodiment, the lamellar gel composition comprised 88 weight % water, 7.3 weight % lipid, 4.4 weight % pentanol and 1.4 weight % PEG-lipid. These composition ranges are by no means limiting and other embodiments exist.

By providing a model system of functional lamellar gel components, one may readily substitute and test new components. In particular, one skilled in the art may utilize a new component and observe changes in macroscopically detectable effects such as multiple phases and viscosity. The effect of the new molecule or molecules in the lamellar gel composition may then be further examined by both small and wide-angle x-ray scattering data as described in Example 1 below.

METHODS OF THE INVENTION

The present invention provides methods for making lamellar gels and methods for controlling the phase state or structure of the gel composition.

In one embodiment for making the lamellar gel, the method comprises mixing a lipid or a surfactant in a sufficient amount so as to form a flexible membrane and then adding in a sufficient amount a multifunctional membrane associating particle which anchors to the membrane and creates highly curved membrane regions. By varying the relative amount of the (1) lipid and (2) membrane associating particle distinct lamellar phases can be generated which include a gel phase characterized by a highly defected microstructure composed of a network of connected membrane bilayers with the membrane associating particle segregated to the high curvature regions resulting in the production of the intermembrane connections.

In another embodiment for making the lamellar gel, the method comprises mixing a lipid or a surfactant in a sufficient amount so as to form a flexible membrane and then adding in a sufficient amount of a multifunctional membrane associating particle which anchors to the membrane and creates highly curved membrane region and then adding a sufficient amount of an agent that reduces the membrane rigidity (14). By varying the relative amount of the (1) lipid and (2) membrane associating particle and (3) agent that reduces the membrane rigidity, distinct lamellar phases can be generated which include a gel phase characterized by a highly defected microstructure composed of a network of connected membrane bilayers with the membrane associating particle segregated to the high curvature regions.

The present invention provides a method for making lamellar gels so that, the amount of water in the gel ranges from approximately 60 to approximately 99%, the amount of membrane forming lipid ranges from approximately 1 to approximately 40 weight % lipid, approximately 0.5 to approximately 20 weight % of the PEG-lipid and approximately 2 to approximately 5 weight % pentanol. These composition ranges are by no means limiting and other embodiments exist.

In one specific embodiment, the present invention provides a method for making a lamellar gel consisting of 90.0 weight % water, 6.0 weight % lipid, 3.46 weight % pentanol and 0.54 weight % PEG-lipid. In yet another embodiment, the present invention provides a method a method for making gel consisting of 83.0 weight % water, 8.4 weight % lipid, 5.7 weight % pentanol and 3.0 weight % PEG-lipid. In yet another embodiment, the present invention provides a method of making gel consisting of 88 weight % water, 7.3 weight % lipid, 4.4 weight % pentanol and 1.4 weight % PEG-lipid. These composition ranges are by no means limiting and other embodiments exist.

As discussed above, the invention provides a method for regulating the structure of a lamellar gel. The method comprises selecting (1) a lipid, surfactant, or lipid/surfactant combination and (2) a multifunctional membrane associating particle. After selection is accomplished the method further comprises determining the amount of the lipid, surfactant, or lipid/surfactant combination and the amount of the membrane associating particle sufficient to regulate the structure of the complex. This determination can be achieved by selecting a characteristic or multiple characteristics of the gel from a group of characteristics.

Selecting a characteristic in the context of the invention means assigning a desired numerical value to the characteristic or characteristics so selected. The characteristics include any of (1) Boltzmann's constant multiplied by temperature ($k_B T$), (2) the volume fraction of the membrane associating particle in the membrane ($\Phi^P_v$), (3) the natural curvature of membrane associating particle ($C^P_O$), (4) volume fraction of water ($\Phi_W$) and (5) an agent that controls the membrane bending rigidity of the gel. In addition to modulating the above characteristics, other characteristics not listed above may be modulated to regulate lamellar gel structure.

The methods of the invention further provide modulating any of the characteristics not selected above so as to achieve the selected characteristic or characteristics. Modulating in the context of the invention means determining the numerical value of the nonselected characteristics in view of the selected characteristics sought to be achieved so as to determine the required amounts of the lipid, surfactant, or lipid/surfactant combination and the multifunctional membrane associating particle sufficient to regulate the structure of the lamellar gel as desired.

After determining the desired amounts, the lipid, surfactant, or lipid/surfactant combination can be combined with the multifunctional membrane associating particle thereby resulting in the lamellar gel having the desired structure.

In one embodiment of the invention, modulating is achieved using the formula:

$$d_{gel} = \frac{2 - 2^{1/2} k_B T / \pi k}{\Phi^P_v C^P_O}$$

In this formula $d_{gel}$ is the distance between neighboring membranes. $k_B T$ is Boltzmann's constant multiplied by temperature (13). $\Phi^P_v$ is the volume fraction of the membrane associating particle in the membrane (e.g., from about 0.001 to about 0.5). $C^P_O$ is the natural curvature of MAP (13). $\Phi_W$ is the volume fraction of water. $\pi$ has a constant value of 3.14 lb. $\kappa$ is the membrane bending rigidity. The range of $\kappa$ values includes 1 $k_B T$ to about 20 $k_B T$.

Alternatively, modulating can be effected using the formula:

$$d_{gel} \alpha \frac{1}{C_{PEG}}$$

In this formula, $$C_{PEG} = \frac{100 \times \#ofPEG-lipidcombination}{total\#oflipids}$$

Further alternatively, modulating can be effected using the formula:

$$d_{gel} \alpha \frac{1}{C_P}$$

In this formula, $$C_P = \frac{100 \times \#ofP}{total\#oflipids}$$

and P is the membrane associating particle.

In accordance with the practice of the present invention, the phase of the lamellar gel composition may be modified by increasing the concentration of one or more of the constituent components such as the membrane associating particle or water. In one embodiment, the method comprises the manipulation of the composition phase by concentrating the levels of the membrane associating particle in sufficient amount such that the composition in the liquid like flowing $L_\alpha$ phase state makes the transition to the gel-like $L_{\alpha g}$ phase (a lamellar gel of the invention). In yet another embodiment, by concentrating the levels of the water in sufficient amount such that the composition in the liquid like flowing $L_\alpha$ phase state makes the transition to the gel-like $L_{\alpha g}$ phase.

In accordance with the practice of the present invention, the phase of the lamellar gel composition may be modified by increasing the concentration of the constituent in a manner that causes the composition to make the transition to multiple phases. In one embodiment, the method of the manipulation of the composition phase occurs by the addition of water where the initial liquid like $L_\alpha$ phase state is made to undergo the transition to form an ordered gel like phase $L_{\alpha g}$ phase and whereupon the further addition of water makes the $L_{\alpha g}$ phase undergo a transition to a disordered state.

In a specific embodiment of the method, a sufficient amount of a component in the lamellar gel composition is determined by the formula:

$$dgel = \frac{2 - 2^{1/2} k_B T / \pi k}{\Phi_v^{PEG} C_O^P}$$

Advantages of the invention: The benefits of being able to make and precisely control the structure of lamellar gels is that it will be possible to tailor make specific structures which have defined chemical and biological activities. Such activities would be useful in the areas of tissue healing or drug delivery applications where a biologically active molecule may be readily incorporated into the gel matrix and manipulated so as to facilitate delivery. Another area of use is in field of cosmetics and hair care products. An aqueous system composed of a rigid lamellar hydrogel that readily incorporates molecules of interest and that loses rigidity and is miscible in water has properties directly applicable for use in hair gels, facial masks, skin creams and the like.

The fluid membrane-based biogels described in this disclosure are useful in the field of functionalized bioactive materials. Because their principle component is lipid and surfactant, "bioactive gels" useful in tissue healing, in chemical sensing, in molecular sieving, or drug delivery applications may be envisioned with activity derived from membrane anchored peptides, proteins, or other drug molecules, and mechanical stability resulting from the polymer-lipid minority component. In analogy to so-called "smart" hydrogels of polymer networks which respond by contracting or expanding to external stimuli such as temperature, solvent, or pH changes, a suitable choice of lipid and polymer-lipid should lead to a different class of smart lamellar hydrogels.

Bioactive gels may also be envisioned comprised of the reconstitution of Bacteriorhodopsin (bR) into the lamellar biogels. bR can function as an optically driven bistable switch at low temperatures. Thus, it may be possible to develop optically addressable materials containing mutant forms of bR which function as high density memories and holographic media at room temperature. Thus, because of the importance of bR in the field of biomaterials research, bR-containing lamellar gels should find much utility. The bioactive gel would combine the optimal mechanical integrity and processability properties of the underlying membrane/polymer structure together with the desirable optical properties of bR.

The following example is presented to illustrate the present invention and to assist one of ordinary skill in making and using the same. The example is not intended in any way to otherwise limit the scope of the invention.

EXAMPLE 1

A class of lamellar biological hydrogels comprised of fluid membranes of lipids and surfactants with small amounts of low molecular weight poly(ethylene glycol)-derived polymer lipids (PEG-lipids) were studied by x-ray diffraction, polarized light microscopy, and rheometry. In contrast to isotropic hydrogels of polymer networks, the membrane-based birefringent liquid crystalline biogels, labeled $L_{\alpha,g}$ (a lamellar gel of the invention) form the gel phase when water is added to the liquid-like lamellar $L_\alpha$ phase (a lamellar layer of lipid and water without MAP or an agent that controls membrane bending rigidity of the gel), which reenters a liquid-like mixed phase upon further dilution. Furthermore, gels with larger water content require less PEG-lipid to remain stable. Although concentrated (~50 weight percent) mixtures of free PEG (molecular weight, 5000) and water do not gel, gelation does occur in mixtures containing as little as 0.5 weight percent PEG-lipid. A defining signature of the $L_{\alpha,g}$ regime as it sets in from the fluid lamellar $L_\alpha$ phase is the proliferation of layer-dislocation-type defects, which are stabilized by the segregation of PEG-lipids to the defect regions of high membrane curvature that connect the membranes.

Gels are viscoelastic materials that normally consist of a solid component dispersed in a liquid, water in the case of hydrogels. Polymer gels (1)—either natural, such as gelatin, or synthetic—contain a polymer network (2), which serves as the solid component and can resist shear. For many biological applications, polymer gels based on high molecular weight poly(ethylene oxide) $[PEO_x(OCH_2CH_2)_n]$ (3) have been used because of their low immunogenicity: the material can be used to coat more immunogenic tissues (1) and materials (4).

Recent studies show that attaching low molecular weight (n<150) PEO (referred to as PEG) to a biological macromolecule (5–8) can dramatically increase blood circulation times. Both peptides and proteins can be protected by covalently attached PEG for in vivo administration of therapeutic enzymes (5), and so-called "Stealth" liposomes (6–8) consisting of closed bilayer shells of phospholipids covered with PEG-lipids hydrophobically anchored to the membrane can be used as a drug carrier system. The inhibition of the body's immune response to these PEG-coated liposomes has been attributed (8) to a polymer-brush-type steric repulsion (9) that has been measured between PEG-coated membranes incorporated both in the chain-frozen membrane phase on a solid substrate (10) and in the chain-melted fluid phase in multilamellar $L_\alpha$ systems (11). In these systems, the emphasis was in the regime where the intermembrane distance $d \leq R_g$, where $R_g$ is the PEG radius of gyration.

In exploring the interactions between PEG-lipid and the chain-melted fluid phase in multilamellar $L_\alpha$ systems, we have discovered a lamellar gel of the invention, i.e., a lamellar hydrogel phase, labeled $L_{\alpha,g}$, in the high water regime of the phase diagram. This gel incorporates no solid phase component. Polarized light microscopy has revealed that this phase is not isotropic and shows liquid crystal-like birefringence. Studies with x-ray diffraction show that the maximum interlayer spacings $d >> R_g$ for this phase (FIG. 1A); a model for the structure of this phase suggests that PEG-lipids stabilizes layer dislocation defects in regions of high membrane curvature (FIG. 1B). Unlike $L_\beta$ gels that incorporate solid membranes (12), a bioactive gel based on fluid membranes could incorporate membrane-embedded proteins that are biologically active, thus providing a way in which to deliver such molecules in a stable gel. An unusual feature of these gels is that they can be formed from a liquid-like flowing $L_\alpha$ phase by adding water and also dissolved back to a flowing two-phase liquid by further addition of water.

The $L_{\alpha,g}$ phase is composed of membranes of DMPC (dimyristoyl phosphatidyl choline), the co-surfactant pentanol, and small amounts of the polymer-lipid PEG-DMPE {1,2-diacyl-sn-glycero-3-phosphoethanolamine-N-[poly(ethylene glycol)]} separated by water.

Figure 2:
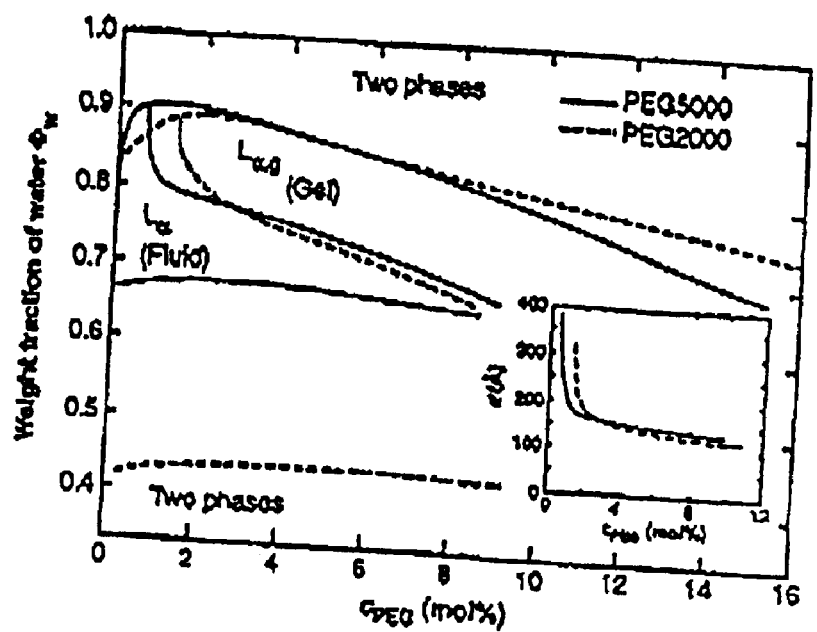
FIG. 2 is a phase diagram for PEG5000-DMPE (solid line) and PEG2000-DMPE (dashed line), plotted in terms of the water weight fraction $\Phi_W$ versus the concentration of PEG-lipid in the total lipid, denoted by $C_{PEG}$ (100×(number of PEG-lipid molecules)/(total number of lipid molecules), where total lipid is DMPC+DMPE.

The PEG-lipid is hydrophobically anchored but free to diffuse within the fluid membrane (FIG. 1a). We investigated two different molecular weights of PEG, 2053 g/mol (PEG2000; n=45 monomers) and 5181 g/mol (PEG5000; n=113) (Avanti Polar Lipids, Alabaster, Ala.). The most dilute gels contained 90.0 weight % water, 6.0 weight % lipid, 3.46 weight % pentanol, and 0.54 weight % PEG5000-DMPE (FIG. 2). In contrast, the conventional solid-membrane $L_\beta$, gels incorporate at most 40 weight % water (12). In principle, addition of PEG-lipid to even more dilute $L_\alpha$ phases ≈99 weight % (13)] would result in extremely dilute lamellar gels.

For both molecular weights of PEG-DMPE, sample viscosity increases dramatically with the onset of gelation, occurring both as a function of increasing PEG-lipid concentration and, unexpectedly, as a function of increasing water concentration. Remarkably, we find an inverse behavior for gelation, with mixtures of larger water content gelling at lower PEG-lipid concentrations. An important finding is the formation of hydrogels containing as low as 0.5 weight % PEG-lipid, which is much smaller than a monolayer coverage of the bilayers. Polymer hydrogels consisting of free PEG at such low concentrations would require molecular weights of PEO of order a million.

The key difference with previous work (11) that allowed us to explore the regime $d \gg R_g$, where the biogel is stable, was the high flexibility of the fluid membranes within which the PEG-lipid was incorporated. Without PEG-lipid, the addition of the co-surfactant pentanol to membranes consisting of DMPC thins the bilayer membrane, which leads to the decrease of its bending rigidity $K \approx k_B T$ (thermal energy) (14). The lamellar $L_\alpha$ phase is then comprised of fluid, highly flexible membranes with interactions dominated by long-range repulsive undulation forces (14–16), giving rise to large intermembrane distances. In our studies, we fixed the ratio of pentanol to lipid molecules at ~4:1, which corresponds to bilayers of thickness $\delta \approx 28$ A(14).

In the case of PEG5000-DMPE, for water weight fraction $\Phi_W < 0.66$, which is below the lower two-phase boundary on the phase diagram (FIG. 2), the stacked bilayers cannot incorporate any PEG5000. This boundary corresponds to an average membrane separation $d_{water}$ 60 Å. For PEG2000-DMPE, the two-phase boundary occurs at $d_{water} \approx 25$ Å. Thus, as a function of increasing water, the one-phase lamellar region is stable when the separation distance is approximately large enough to accommodate the swollen PEG polymer. The maximum spacings where the lamellar regions remain one-phase correspond to $d_{water} = 390$ Å≈6 Rg for PEG5000-DMPE $d_{water} = 286 \approx$ Å≈$SR_R$ for PEG2000-DMPE (FIG. 2, inset) [for PEG-lipid in lipid membranes, Rg has been measured to be about 35 and 62 Å for PEG2000 and PEG5000, respectively (10, 11)].

At water concentrations $\Phi_W > 0.66$ and low PEG-lipid concentrations, we observe a low viscosity, lamellar liquid-crystal (LC) $L_\alpha$ phase qualitatively similar in appearance to $L_\alpha$ samples not incorporating PEG-lipid. However, mixtures changed from a flowing to a gelling lamellar phase upon the addition of either PEG-lipid or water (FIG. 2). Using approximate numbers for the PEG radii of gyration together with those for the areas of lipid and co-surfactant molecules (10, 11), we estimated the concentration where the mushroom-shaped PEG-lipid first covers a flat membrane before any overlap of the polymer chains occurs to be about 3 mol % for PEG5000-DMPE and 8 mol % for PEG2000-DMPE. The transition to the gel phase then occurs in PEG-lipid concentrations below the brush regime, where the polymer does not fully coat the membrane. Thus, the direct interactions between the PEG on opposing layers can be ruled out as a mechanism for gelation. In addition, the gel samples can be prepared in brine (for example, 0.5 M NaCl), which rules out long-range electrostatic interactions (17) in gel formation (18).

Figures 3A, 3B, 3C, 3D:
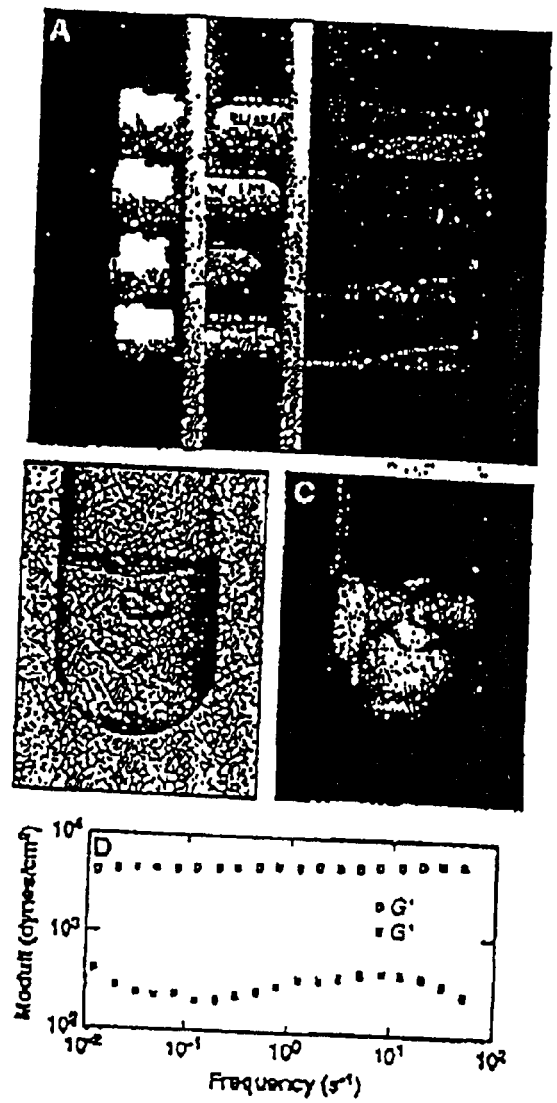
FIG. 3A is four samples each with a PEG2000-DMPE concentration of 6.06 mol % but increasing water content.
FIG. 3B is a lamellar gel showing non-spherical bubbles. Bubbles like these have lasted more than 6 months.
FIG. 3C is the same gel sample from FIG. 3A viewed between crossed polarizers, showing liquid crystalline defects.
FIG. 3D is dynamic elastic moduli for the $\Phi_W$=0.78 gel sample as a function of frequency (measured with a cone and plate rheometer). These data are typical of the gel samples in that the elastic storage modulus G' is substantially greater than the viscous loss modulus G" over the four decades of frequency measured.

We placed four mixtures of varying $\Phi_W$ [spanning three regions of the phase diagram (FIG. 2)] in glass tubes tilted to allow flow (FIG. 3A). As $\Phi_W$ increased initially from 0.45 to 0.68, the sample flowed more easily, which is the typical expected behavior observed in complex fluids as a function of solvent dilution (13). Upon further increase in the water fraction, the sample gelled at $\Phi_W \approx 0.71$; elasticity dominated, and the mixture, which abruptly ceased to flow, had properties of a weak solid. Mixtures of free PEG (molecular weight, 2000) and water do not gel, even when extremely concentrated (for example, as large as 90 weight % PEG). As we added more water, the mixture dissolved into a liquid-like two-phase region (FIG. 3A, top tube). The $L_{\alpha g}$ phase is a physical gel rather than a traditional chemical gel, which has permanent covalent-bond cross-links (2).

The gel samples can sustain arbitrary shapes against surface tension and gravity for indefinite periods. The non-spherical stable bubbles (FIG. 3B) show that the sample has a yield stress resisting surface tension forces, as expected for a gel. The real (storage elasticity modulus G') and imaginary (loss modulus G" α viscosity) parts of the dynamic moduli were measured (19). As a function of increasing PEG2000-DMPE concentration, G'/G" varied between 4 and 20 in the gel phase (FIG. 3D).

The LC nature of the $L_{\alpha g}$ biogels distinguishes them from most natural- and biopolymer-based hydrogels (1, 2). When viewed between crossed polarizers (FIG. 3C), the samples are birefringent and LC defects (20) are visible on a millimeter scale.

Figures 4A, 4B, 4C, 4D, 4E:
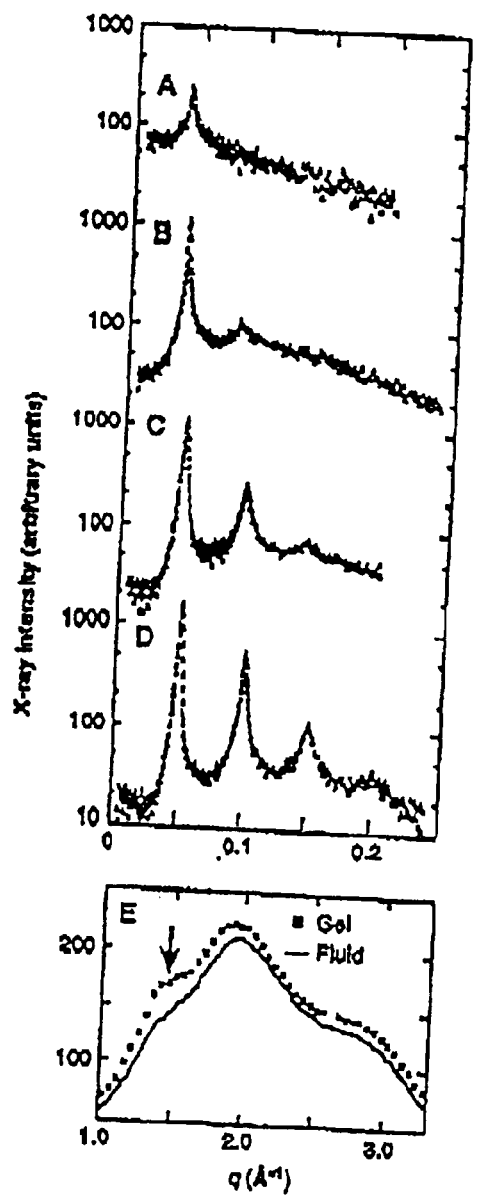
FIG. 4A–4D is synchrotron x-ray scattering data on four samples along an increasing PEG2000-DMPE line: (A) $c_{PEG}$=0 MOL %, $\Phi_W$=0.80, d=155 Å; (B) $c_{PEG}$=2.9 mol %, $\Phi_W$=0.78, d=147 Å; (C) $c_{PEG}$=7.8 MOL %, $\Phi_W$=0.75, d=133 Å; (D) $c_{PEG}$=15.5 mol %, $\Phi_W$=0.70, d=127 Å.
FIG. 4(E) is an in-plane scan for the $c_{PEG}$=0 mol % (fluid) and 7.8 mol % (gel) samples, showing the liquid-like chain interference peak at q=1.5 Å$^{-1}$ (arrow) and the two water peaks at 2 and 2.7 Å$^{-1}$.

Small-angle x-ray powder scans (21), corresponding to the (001) peaks of the lamellar structure, are shown for four mixtures along a line of increasing PEG2000-DMPE concentration in the fluid (FIG. 4, A and B) and gel (FIG. 4, C and D) regions. The data shown are in mixtures where the total weight fraction of the hydrophilic portion of the multilayer phase, consisting of water and the water-soluble part of PEG-lipid ($\Phi_W + \Phi_{PEG}$), was kept constant at 0.8 (with $\Phi_W$ varying between 0.8 and 0.7) as $c_{PEG}$ (mole concentration of PEG-lipid) was increased. This observed behavior where the addition of PEG-lipid correlates with the emergence of higher harmonics in the scattering profile, is typical for both PEG2000-DMPE and PEG5000-DMPE. In a fluid lamellar phase (that is, both $L_\alpha$ and $L_{\alpha g}$), the onset of the higher harmonics is an indication of the stiffening of the bulk compression modulus B (14, 16, 20). This suggests that PEG-coated membranes in a flexible multilayer system experience an enhanced repulsive interaction (23) as a function of increasing $c_{PEG}$, which is consistent with the measured increase in B.

The value of B increases smoothly as $c_{PEG}$ increases and the gel forms. The onset of the harmonics depends on $c_{PEG}$ but is essentially independent of the water content $\Phi_W$ (or d); that is, harmonics do not emerge as dilution with water forms the gel. Thus, the increase in B is not directly related to the gel transition. Experiments at higher angles (FIG. 4E) verify that the interference peak at $q \approx 1.5$ Å$^{-1}$ caused by interactions between the lipid chains remains liquid-like in both the $L_\alpha$ and $L_{\alpha g}$ regimes; thus, the addition of PEG-lipid does not affect bilayer fluidity. Unlike $L_\beta$ gels, gelation is not a result of in-plane chain ordering (12).

Figures 5A, 5B, 5C, 5D, 5E:
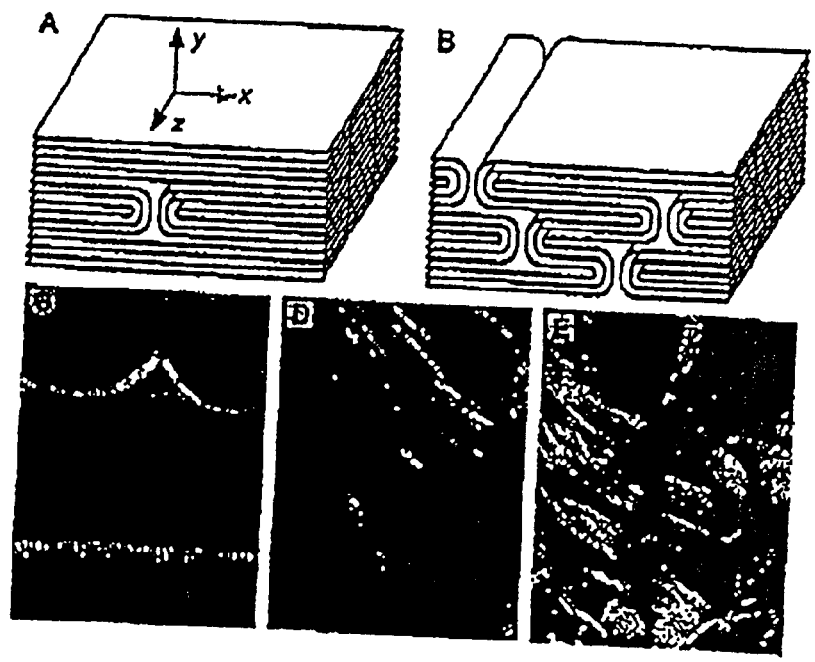
FIG. 5 is a real space structure of defects in the (A) fluid $L_f$ and (B) gel $L_{\alpha,g}$ phases. For simplicity, we show in (A) a defect pair with opposite Burgers vectors each of strength 6. Unequal Burgers vectors are expected with nonuniform sample thickness. In the $L_\alpha$ phase, the defects can be annealed, whereas in the $L_{\alpha,g}$ phase, the defects cannot be annealed. (C through E) Optical microscopy pictures of defects in PEG2000-DMPE samples along a line of increasing PEG-lipid concentration (with $\Phi_W+\Phi_{PEG}$=0.8).

The onset of gelation is marked by a distinct change in the defect structure observed in polarized light microscopy (24). Samples in the fluid $L_\alpha$ regime primarily exhibit homeotropic (lamellae parallel to the glass surfaces) alignment broken by the typical "oily streak" defects characteristic of lamellar phases with melted chains (FIG. 5C; xy plane). The basic form of the oily streak has been described previously in terms of a disclination-pair defect (FIG. 5A), each part of strength +1/2 (25). Striations along the length of the defect (z axis) can be attributed to undulations of the defect axis in and out of alignment with axes of the crossed polarizers (25). The defect structure can also be described in terms of two opposite edge dislocations with large Burgers vectors (20, 25).

As the transition to the $L_{\alpha g}$ region is approached, we observe a proliferation of these line defects, which are now significantly thinner (FIG. 5D). A cut through the sample exposing the xy plane normal to the line defects running along the z axis (FIG. 5B) would have a dense packing of edge-dislocation pairs. The closure of an edge-dislocation pair would produce a defect loop. The ends of the loop would consist of multilayers with layer normal along z parallel to the defect lines. Within this "whispy" texture, which is a common textural observation in the $L_{\alpha g}$ phase, regions of densely packed and highly aligned line defects (FIG. 5E) provide evidence of what appears to be a nematic ordering of line defects in macroscopically large regions of the sample (26). On millimeter length scales, nematic-like (20) Schlieren defects are apparent (FIGS. 3C and 5E); that is, nematic disclination defects of the (edge-dislocation) line defects. In contrast to the $L_\alpha$ phase mixtures, in which the defects may be annealed, the densely packed defected $L_{\alpha g}$ texture cannot be annealed and is inherent to the gel phase.

A simple model of the lamellar fluid-gel transition is described by the softening of the free energy of line defects and their consequent proliferation as observed experimentally. This model is qualitatively consistent with the phase behavior, where gelation in mixtures with larger interlayer spacing (larger water content) occurs at smaller PEG-lipid concentrations. For simplicity, we consider the elastic costs of the simplest defect line consisting of an edge-dislocation pair of opposite Burgers vector of strength 2 (FIG. 1B, bottom). The membranes consist primarily of two components. The bare membrane component (DMPC and pentanol) has a natural radius of curvature $\underline{C_O^L=0}$ (FIG. 1A, top right); that is, fluid membranes with this mixture are know to form stable lamellar $L_\alpha$ phases (13, 16). The PEG-lipid component has a finite natural radius of curvature $\underline{C_O^P>0}$ (FIG. 1A, top right) and is known to stabilize vesicles (7, 8, 11). At low PEG-lipid concentrations, the two components are uniformly mixed (FIG. 1B, top). As the PEG-lipid concentration increases, a frustration is built where the different components compete for varying membrane curvature. The formation of stable edge-dislocation defect lines observed experimentally satisfies both components where the regions of high curvature membrane are the aggregation sites of the PEG-lipid component (FIG. 1B, bottom). Two different pathways could be followed. Along path (i) (FIG. 1B), in-plane phase separation, which has been observed in PEG-lipid monolayers spread at an air-water interface (27), precedes stable curvature (defect) formation. Along path (ii), the coupling between the membrane curvature and concentration components may lead to a curvature-induced in-plane phase separation that would also result in stable defects consistent with recent theoretical work (28).

The elastic cost of forming a line defect of length L with edge curvature C=2/d (that is, the two half cylinders shown in FIG. 1B, bottom) is given by the Helfrich elastic energy of fluid membranes (15) $E_d=0.5\ \pi\kappa Ld\ (C-C_O)^2$ where $C_O= \underline{\Phi_v^{PEG}C_O^P},\Phi_v^{PEG}$ is the volume fraction of PEG-lipid in the membrane, and P is the membrane bending rigidity. The entropy gained in forming the line defect is given by $TS=k_BTL/\xi_p$, where $\xi=\pi d\kappa/k_BT$ is the persistence length (29) of the cylindrical membrane. The softening of the line free energy $E_d-TS=0$ then leads to the simple relation for the proliferation of line defects at the lamellar fluid-gel transition $$dgel = \frac{2-2^{1/2}k_BT/\pi k}{\Phi_v^{PEG}C_O^P} \tag{1}$$

Because $\underline{\Phi_v^{PEG}}$ roughly scales as $C_{PEG}\ V_{PEG1}$ where $V_{PEG}=N^V{}_{PEG1}$ (N=degree of polymerization, $v_{PEG}$=volume of a monomer), Eq. 1 is qualitatively consistent with our experimental phase diagram, where $d\alpha 1/c_{PEG}$(gel) (FIG. 2, inset). This simple model not only contains the inverse relation between water and polymer content required for gelation but also gives the correct qualitative trend in the scaling behavior of the PEG2000-DMPE and PEG5000-DMPE systems. The natural radius of curvature $\underline{C_O^P}$ can be estimated from the result for an asymmetric block copolymer at a spherical vesicle interface calculated previously with $\underline{C_O^P}\alpha 1/N^{2/3}$ (30). The scaling dependence of the interlayer spacing at the gel transition then behaves as $d_{gel}\alpha 1/\Phi_v^{PEG}C_O^P\alpha 1/N^{1/3}$. This result is qualitatively consistent with the phase diagram (FIG. 2, inset), where as we increase d at a constant PEG-lipid concentration<2 mol %, PEG5000-DMPE gels before PEG2000-DMPE . The schematic in FIG. 1B (bottom) gives a simple description of the model: Larger water fractions lead to a larger spacing d and consequently a smaller curvature (joining opposing bilayers), which in turn, requires less PEG-lipid.

The gel phase is then characterized by a highly defected microstructure comprised of a network of connected membrane bilayers with the PEG-lipid segregated to the high curvature regions (FIG. 1B), which on a semimacroscopic length scale leads to domains of random layer orientation (FIG. 5B). Recent theoretical work (31) has shown that the random orientation of domains in lamellar block copolymers, structurally similar to lamellar phases of membranes, will lead to elasticity and thus gel-like behavior because domains that have their layer normals with a finite projection along the flow direction will resist shear, because of the energetically unfavorable tilting of layers.

Because the principal component of these fluid membrane-based hydrogels is lipid and surfactant, "bioactive gels" useful in tissue healing or drug delivery applications (4, 7, 8) may be envisioned that derive their activity from membrane-anchored peptides, proteins, or other drug molecules and their mechanical stability from the polymer-lipid minority component. Alternatively, in analogy to so-called "smart" hydrogels of polymer networks, which respond by contracting or expanding to external stimuli such as temperature solvent, or pH changes (1, 32) a suitable choice of lipid and polymer-lipid should lead to a different class of smart lamellar hydrogels.

FIG. 1A is a schematic of two undulating fluid membranes [composed of DMPC and co-surfactant pentanol (single chain)] with PEG-lipid hydrophobically anchored but freely diffusing within the membrane. FIG. B is a schematic of two paths that would form defects, with the laterally phase separated PEG-lipid residing in, and stabilizing, the regions of high curvature. The interlayer spacing is $d=\beta_\delta+d_{water}$, where $\delta$ is the membrane thickness and $d_{water}$ is the separation between layers containing water and the hydrophilic PEG component.

FIG. 2 is a phase diagram for PEG5000-DMPE (solid line) and PEG2000-DMPE (dashed line), plotted in terms of the water weight fraction $\Phi_W$ versus the concentration of PEG-lipid in the total lipid, denoted by $C_{PEG}$ (100×(number of PEG-lipid molecules)/(total number of lipid molecules), where total lipid is DMPC+DMPE. The lipid-to-pentanol weight ratio was 2.0±0.25. Note that the gel regime is accessed by increasing either the PEG-lipid concentration or the water concentration. (Inset) Comparison of the fluid-gel transition lines for PEG5000-DMPE and PEG2000-DMPE, plotted with the interlayer spacing $d \approx d_{water}+\delta$ instead of $\Phi_W$.

FIG. 3A is four samples each with a PEG2000-DMPE concentration of 6.06 mol % but increasing water content. From bottom to top: $\Phi_W$=0.45 (lamellar interlayer spacings d=55 Å, $L_\alpha$ fluid), 0.68 (d=110 Å, $L_\alpha$ fluid), 0.78 (d=165.4 Å, $L_{\alpha,g}$ gel), and 0.95 (two-phase liquid-like). The test tubes are 13 mm in diameter. FIG. 3B is a gel sample showing non-spherical bubbles. Bubbles like these have lasted more than 6 months. FIG. 3C is the same gel sample viewed between crossed polarizers, showing liquid crystalline defects. FIG. 3D is dynamic elastic moduli for the $\Phi_W$=0.78 gel sample as a function of frequency (measured with a cone and plate rheometer). These data are typical of the gel samples in that the elastic storage modulus G' is substantially greater than the viscous loss modulus G" over the four decades of frequency measured.

FIG. 4A–4D is synchrotron x-ray scattering data on four samples along an increasing PEG2000-DMPE line: (A) $c_{PEG}$=0 MOL %, $\Phi_W$=0.80, d=155 Å; (B) $c_{PEG}$=2.9 mol %, $\Phi_W$=0.78, d=147 Å; (C) $c_{PEG}$=7.8 MOL %, $\Phi_W$=0.75, d=133 Å; (D) $c_{PEG}$=15.5 mol %, $\Phi_W$=0.70, d=127 Å. The first two samples are in the $L_\alpha$ fluid, and the last two are in the $L_{\alpha,g}$ gel regime, which sets in around $c_{PEG}$=4.0±0.25 mol % and $\Phi_W$=0.76±0.02 along this line. The emergence of harmonics with added polymer lipid indicates an increase in the intermembrane repulsion. (E) In-plane scan for the $c_{PEG}$=0 mol % (fluid) and 7.8 mol % (gel) samples, showing the liquid-like chain interference peak at q=1.5 Å$^{-1}$ (arrow) and the two water peaks at 2 and 2.7 Å$^{-1}$.

FIG. 5 is a real space structure of defects in the (A) fluid $L_\alpha$ and (B) gel $L_{\alpha,g}$ phases. For simplicity, we show in (A) a defect pair with opposite Burgers vectors each of strength 6. Unequal Burgers vectors are expected with nonuniform sample thickness. In the $L_\alpha$ phase, the defects can be annealed, whereas in the $L_{\alpha,g}$ phase, the defects cannot be annealed. (C through E) Optical microscopy pictures of defects in PEG2000-DMPE samples along a line of increasing PEG-lipid concentration (with $\Phi_W+\Phi_{PEG}$=0.8). All photographs are of samples in 0.2-mm-thick flat rectangular glass capillaries observed between crossed polarizers. (C) Sample with $c_{PEG}$=1.1 mol % and $\Phi_W$=0.79 showing the oily streak defects typical of $L_I$ phases. (D) Mixture with $C_{PEG}$=4.53 mol % and $\Phi_W$=0.78 in the gel phase (gel transition at $c_{PEG}$=4.0±0.25 mol % and $\Phi_W$=0.76±0.05 along this line). The proliferation of the line defects is evident. (E) Defects in a sample with $C_{PEG}$=4.2 mol % and $\Phi_W$=0.77 in the gel phase, which in addition to the line defects also shows dark brushes attributable to disclinations of the defect lines.

References

1. See, for example, D. DeRossi, K. Kajiwara, Y. Osada, A. Yamauchi, Eds., *Polymer Gels: Fundamentals and Biomedical Applications* (Planum, New York, 1991).
2. In a polymer chemical gel, the network consists of covalent cross-links. In a polymer physical gel, the network is formed either through temporal enlargements or interactions (for example, electrostatic, van der Wasis, hydrogen-bonding, or hydrophobic interactions) between macromolecular sections [see, for example, S. B. Ross-Murphy, In (1), p. 21].
3. See, for example, F. E. Bailey Jr. and J. V. Koleske, Eds., *Poly (Ethylene Oxide)* (Academic Press, New York, 1976).
4. N. A. Peppas and R. Langor, *Science* 263, 1715 (1994).
5. See, for example, V. H. L. Lee, Ed., *Peptide and Protein Drug Delivery* (Dekker, New York 1991); E. Marshall, *Science* 269, 1050 (1995).
6. T. M. Allen and A. Chonn, *FEBS Lett.* 223, 42 (1987); A. Gabizon and D. Papahadjopoulos, *Proc. Natl. Acad. Sci. U.S.A.* 85, 6949 (1986).
7. D. D. Lasic, *Liposomes: From Physics to Applications* (Elsevier, Amsterdam, 1993).
8. See, for example, D. D. Lasic and D. Papahadjopoulos, *Science* 267, 1275 (1995); D. D. Lasic and F. J. Martin, Eds., *Stealth Liposomes* (CRC Press, Boca Raton, Fla. 1995).
9. S. Alexander, *J. Phys. France* 38, 977 (1977); P.-G. De Gennes, bld. 37, 1443 (1976); *Macromolecules* 13, 1069 (1980); S. T. Milner, *Science* 251, 905 (1991).
10. T. L. Kuhl, D. E. Lackband, D. D. Lasic, J. N. Israelachvie, *Biophys. J.* 66, 1479 (1994).
11. D. Needham, T. J. McIntosh, D. D. Lasic, *Biochim. Biophys. Acta* 1108, 40 (1992); A. K. Kamworthy, K. Hristova, D. Needham, T. J. McIntosh, *Biophys. J.* 68, 1921 (1995).
12. A. Tardieu, V. Luzzati, F. C. Reman, *J. Mol. Biol.* 75, 711 (1973); D. M. Small, in *The Physical Chemistry of Lipids*, vol. 4 of *Handbook of Lipid Research*, D. M. Small, Ed. (Plenum, New York, 1986); G. S. Smith, E. B. Sirota, C. R. Safinya, N.A. Clark, *Phys. Rev. Lett.* 60, 813 (1988); G. S. Smith, E. B. Sirota, C. R. Safinya, R. J. Planc, N. A. Clark, *J. Chem. Phys.* 92, 4519 (1990).
13. See, for example, A. Ben-Shaul, W. M. Gelbert, D. Roux, Eds., *Micelles, Membranes, Microemulsions and Monolayers* (Springer-Voriage, New York, 1994).
14. C. R. Safinya, E. B. Sirota, D. Roux, G. S. Smith, *Phys. Rav. Latt.* 62, 1134 (1989).
15. W. Heifrich, *Z. Naturtorsch.* A 33, 305 (1978); *ZNaturforach*, C 28, 693 (1973).
16. C. R. Safinya et al., *Phys. Rev. Lett.* 57 2718 (1986).
17. Each PEG-lipid has one negative charge; however, the membrane charge density is very low because of the low PEG-lipid concentration.
18. D. Roux and C. R. Safinya, *J. Phys. France* 49, 307 (1988).
19. Constant-stress oscillatory shear-strain experiments were carried out with a Rheometrics dynamic stress rheometer, model 1710C.
20. P.-G. DeGennes and J. Prost, *The Physics of Liquid Crystals* (Clarendon, Oxford, ed. 2. 1993).
21. High-resolution x-ray scattering structural studies were carried out at the Stanford Synchrotron Radiation Laboratory on the wiggler beamlines 6-2 and 10-2.
22.
23. The interaction results from undulation-induced anti-depletion forces.
24. Samples word prepared in flat glass capillaries measuring 0.2 mm, 0.1 mm, and 0.05 mm thick, used as supplied by in Vitro Dynamics.
25. S. A. Asher and P. S. Pershan, *Biophys. J.* 27.393 (1979); M. B. Schneider and W. W. Wobb, *J. Phys. France* 45, 273 (1984); P. Boltenhagen, O. D. Lavrentovich, M. Kiernan, *Phys. Rev. A* 46, 1743 (1992).
26. On occasion, the gel mixture contained a small amount of "spherulite"-type defects (that is, focal conic domains with positive Gaussian curvature (25); the "whispy" fine defects that dominate have negative Gaussian curvature).

27. B. H. Cao and M. W. Kim, *Faraday Discuss.* 98, 245 (1994).
28. U. Seifert, *Phys. Rev. Lett.* 70, 1335 (1993); T. Kawakatau, D. Andelman, K. Kawasaki, T. Tariguchi, *J. Phys. II France* 3, 971 (1993), and references therein.
29. W. Helfrich and W. Harbich, *Chem. Scr.* 25, 2, (1985).
30. Z.-G. Wang and S. A. Safran, *J. Phys. France* 51, 185 (1990).
31. K. Kawasaki and A. Onuki, *Phys. Rev. A* 42, 3664 (1990).
32. F. Ilmain, T. Tenaka, E. Kokufuta, *Nature* 349, 400 (1991); E. S. Matsu and T. Tanaka, Ibid. 356, 482 (1992); Y. Osada and S. B. Ross-Murphy, *Sci. Am.* 268, 82 (May 1993); Z. Hu, X. Zhang, Y. Li, *Science* 269, 525 (1995).

What is claimed is:

1. A lamellar lipid gel comprising:
   (i) a membrane having a surfactant, lipid, or a combination thereof,
   (ii) a multifunctional membrane-associating particle (MAP) which anchors to the membrane, and
   (iii) a membrane bending rigidity reducing reagent.

2. The lamellar gel of claim 1, wherein the membrane bending rigidity reducing reagent is an alcohol.

3. The lamellar gel of claim 2, wherein the alcohol is butanol, pentanol, hexanol, heptanol, octanol, nonanol or a biologically derived alcohol.

4. The lamellar gel of claim 1 further comprising Bacteriorhodopsin.

5. The lamellar gel of claim 1, wherein the lipid is dimyristol phosphatidyl choline.

6. The lamellar gel of claim 1, wherein the surfactant is bis(2-ethyl-hexyl)sulfasuccinate.

7. The lamellar gel of claim 1, wherein the surfactant is pentaethyleneglycol dodecyl ether.

8. The lamellar gel of claim 1, wherein the membrane associating particle is a polymer-lipid combination.

9. The lamellar gel of claim 8, wherein the polymer-lipid combination is PEG-1,2-diacyl-sn-glycero-3-phosphoethanolamine.

10. The lamellar gel of claim 9, wherein the PEG-1,2-diacyl-sn-glycero-3-phosphoethanolamine is PEG-2000.

11. The lamellar gel of claim 9, wherein the PEG-1,2-diacyl-sn-glycero-3-phosphoethanolamine is PEG-5000.

12. The lamellar gel of claim 1, wherein the lipid, surfactant, or lipid/surfactant combination of (i) is in an amount from approximately 1–40 weight %, the MAP of (ii) is in an amount from approximately 0.5–20 weight % and the membrane bending rigidity reducing reagent of (iii) is in an amount from approximately 2–10 weight %.

13. The lamellar gel of claim 1, wherein the lipid, surfactant, or lipid/surfactant combination is in an amount from approximately 1–40 weight %, the membrane associating particle is approximately 0.5–20 weight % and the membrane bending rigidity reducing reagent is approximately 2–10 weight %.

14. A lamellar gel comprising 90.0 weight % water, 6.0 weight % lipid, 3.46 weight % pentanol and 0.54 weight % PEG-lipid.

15. A lamellar gel comprising 83.0 weight % water, 8.4 weight % lipid, 5.6 weight % pentanol and 3.0 weight % PEG-lipid.

16. A lamellar gel comprising 88 weight % water, 7.3 weight % lipid, 3.3 weight % pentanol and 1.4 weight % PEG-lipid.

17. The lamellar gel of claim 1, wherein the MAP is in an amount from approximately 0.5–20 weight %.

18. The lamellar gel of claim 1, wherein the lipid, surfactant, or lipid/surfactant combination is in an amount from approximately 1–40 weight %.

19. The lamellar gel of claim 1, wherein the membrane bending rigidity reducing reagent is a co-surfactant.

20. The lamellar gel of claim 1, wherein the co-surfactant is an n-alcohol with 4 to 9 carbon molecules.

21. The lamellar gel of claim 20, wherein the n-alcohol is a pentanol.

* * * * *